US00PP19536P2

(12) United States Plant Patent
Korlipara

(10) Patent No.: US PP19,536 P2
(45) Date of Patent: Dec. 2, 2008

(54) ***COREOPSIS* PLANT NAMED 'TAHITIAN SUN'**

(50) Latin Name: *Coreopsis*
Varietal Denomination: Tahitian Sun

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/901,038

(22) Filed: Sep. 13, 2007

(51) Int. Cl.
*A01H 5/00* (2006.01)

(52) U.S. Cl. ..... Plt./417

(58) Field of Classification Search ..... Plt./417
See application file for complete search history.

(56) References Cited

PUBLICATIONS

U.S. Appl. No. 11/901,047, filed Sept. 13, 2007, Korlipara.

*Primary Examiner*—June Hwu
(74) *Attorney, Agent, or Firm*—Klarquist Sparkman, LLP

(57) ABSTRACT

A new and distinct *Coreopsis* plant named 'Tahitian Sun' characterized by prolific, large, bicolor rust red and gold daisy-type flowers, grass green foliage, very free branching and flowering, long bloom time, and a mounding habit.

1 Drawing Sheet

Figure 1:
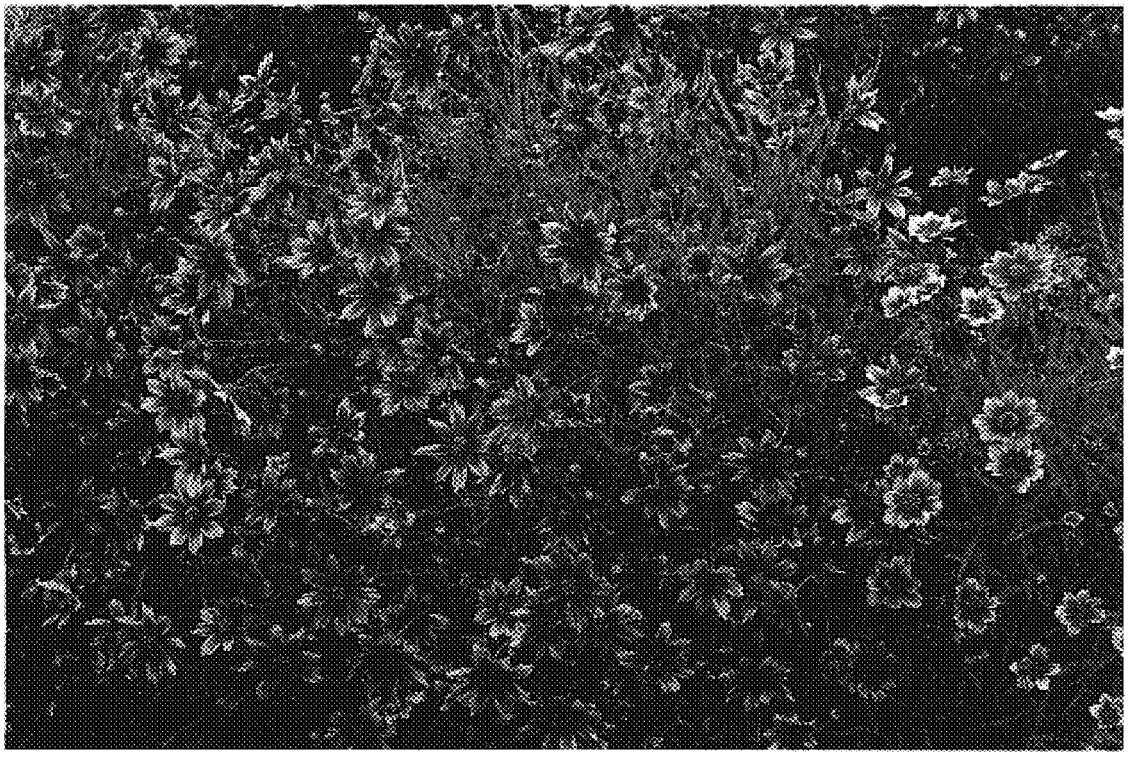

Botanical denomination: *Coreopsis* spp.
Variety designation: 'Tahitian Sun'.

BACKGROUND OF THE INVENTION

The present invention relates to a new and distinct hybrid of *Coreopsis* and given the cultivar name 'Tahitian Sun'. *Coreopsis* is in the family Asteraceae. This new cultivar originated from a tissue culture mutation from *Coreopsis* 'Gold Nugget' (U.S. Plant patent application Ser. No. 11/901,047.

SUMMARY OF THE INVENTION

The following traits have been repeatedly observed and are determined to be the unique characteristics of the new variety. These characteristics in combination distinguish *Coreopsis* 'Tahitian Sun' as a new and distinct cultivar:

1. large, daisy-type flowers that grow to 4.3 cm in diameter;
2. unique, rust red and gold bi-colored ray florets;
3. grass green foliage;
4. very free branching;
5. very free flowering;
6. long bloom time;
7. a mounding habit.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a nine-month-old *Coreopsis* 'Tahitian Sun' growing in the ground in the trial field in August 2007, in Canby, Oreg.

DETAILED PLANT DESCRIPTION

The following is a detailed description of the new *Coreopsis* cultivar based on observations of a nine-month-old specimen growing in the ground in full sun under typical outdoor conditions in the trial fields in August 2007, in Canby, Oreg. Canby is Zone 8 on the USDA Hardiness map. Temperatures range from a high of 95 degrees F in August to a low of 32 degrees F in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zones 7 to 9.
- *Size.*—50 cm wide and 30 cm tall to top of inflorescences.
- *Form.*—Mount.
- *Vigor.*—Excellent.
- *Roots.*—Fibrous, Grey Brown 199D, stems root easily from stem cuttings.

Stem:
- *Type.*—Ascending.
- *Size.*—30 cm tall and 4 mm wide.
- *Internode length.*—5 to 50 mm.
- *Surface.*—Glabrous.
- *Color.*—Green 137A.

Leaf:
- *Type.*—Simple.
- *Shape.*—Linear.
- *Arrangement.*—Opposite.
- *Length.*—Grows to 8 cm.
- *Width.*—4 mm.

*Margins.*—Entire.

*Apex.*—Acute.

*Base.*—Attenuate, clasping.

*Surface texture.*—Glabrous on both sides.

*Venation.*—Pinnate.

*Color.*—Top side Yellow Green 147A, bottom side Yellow Green 147B.

Inflorescence:

*Type.*—Long stalked terminal heads of daisy type inflorescences.

*Peduncle.*—5 to 90 cm long, 1 mm wide, glabrous, Yellow Green 147B.

*Size.*—Grows to 4.3 cm wide and 13 mm deep.

*Immature.*—10 mm long and 5 mm wide, ovoid, glabrous, Grey Brown 199C on top half with Greyed Purple 187A on the tip and Yellow Green 146A on bottom half.

*Receptacle.*—Bowl shaped, 5 mm wide and 5 mm deep, Green 137A.

*Phyllary.*—In two series, 8 lobes, stellate; inner series grows to 12 mm wide and 7 mm deep, lobes reflex, ovate, entire, acute, glabrous, 7 mm long and 3 mm wide, on both sides top half Yellow Green 152C tipped with Greyed Purple 183A, bottom half Yellow Green 147A; outer series with 5 to 7 lobes, grows to 7 mm wide and 4 mm deep, glabrous, lobes lanceolate, entire, acute, 3 mm long and 1.5 mm wide, Green 137A on both sides.

*Bloom period.*—June through September in Canby, Oreg.

*Fragrance.*—Light, Chrysanthemum-like.

*Lastingness.*—Each inflorescence lasts about 7 to 10 days.

Florets:

*Type.*—Composite.

*Ray florets.*—8 with no stamen or pistil, oblanceolate with the tip usually three lobed with lobes obtuse and the central lobe the longest, entire, grows to 22 mm long, 8.5 mm wide, glabrous on both surfaces, claw 1.5 mm long; color topside on a young inflorescence the bottom half Greyed Purple 187A bleeding into Yellow Orange 17A on the top half; with maturity, the bottom half lightens to between Red 46A and Greyed Purple 187B with the top half Greyed Orange 163A from the blending; bottom side Greyed Yellow 162A.

*Disc.*—Conic, deeper with maturity, 5 mm wide and becoming 4 mm deep with maturity, Greyed Purple 187B when in bud, opening to Greyed Orange 163A with a background of Black 202A.

*Disc florets.*—About 65 in number, 9 mm long and 1 mm wide, corolla 4 mm long, tubular, 4 lobed, lobes entire, acute, Greyed Purple 187C, tube Yellow 11C; pistil 1, 7 cm long, ovary 1.5 mm long, Green Yellow 1D, style 6 mm long, extruding, with 2-branched stigma, stigma Yellow Orange 23A and style Green Yellow 1D; stamen 5, 2 mm long, filaments 1.5 mm long, Black 202A, anthers 0.5 mm long, Black 202A, pollen none.

Seed: None produced.

*Fertility.*—Infertile.

Disease and pests: *Coreopsis* are susceptible to mildew and fungal spots. No resistance is known for this variety.

COMPARISONS TO SIMILAR *COREOPSIS*

Compared to *Coreopsis* 'Gold Nugget' (U.S. Plant Pat. No. 18,184), the mother plant, the new variety has ray florets of bicolor rust red with gold tips rather than bright yellow with a red center.

Compared to Coreopsis 'Autumn Blush' (U.S. Plant patent application Ser. No. 11/452,687) the new variety has a much lighter yellow ray floret color.

I claim:

1. A new and distinct *Coreopsis* plant as herein illustrated and described.

* * * * *

UNITED STATES PATENT AND TRADEMARK OFFICE

CERTIFICATE OF CORRECTION

PATENT NO. : PP 19,536 P2
APPLICATION NO. : 11/901038
DATED : December 2, 2008
INVENTOR(S) : Harini Korlipara It is certified that error appears in the above-identified patent and that said Letters Patent is hereby corrected as shown below:

Column 1, line 10, "11/901,047." should be --11/901,047).--.

Column 2, line 23, "Mount" should be --Mound--.

Column 3, line 11, "5 to 90 cm" should be --5 to 9 cm--.

Column 4, lines 29-30, "(U.S. Plant Pat. No. 18,184)" should be --(U.S. Plant Patent Application No. 11/901,047)--.

Column 4, lines 33-34, "(U.S. Plant patent application Ser. No. 11/452,687)" should be --(U.S. Plant Patent No. 18,184)--.

Signed and Sealed this

Twenty-fourth Day of February, 2009

John Doll

JOHN DOLL
*Acting Director of the United States Patent and Trademark Office*